(12) United States Patent
Moore et al.

(10) Patent No.: US 8,788,280 B2
(45) Date of Patent: Jul. 22, 2014

(54) CONVERTING MEDICATION CLAIMS TO ACTIVE MEDICATIONS

(75) Inventors: Matthew J. Moore, Olathe, KS (US); Mallika Edwards, Fairway, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 1537 days.

(21) Appl. No.: 12/020,368

(22) Filed: Jan. 25, 2008

(65) Prior Publication Data

US 2008/0294464 A1  Nov. 27, 2008

Related U.S. Application Data

(60) Provisional application No. 60/886,744, filed on Jan. 26, 2007.

(51) Int. Cl.
*G06Q 50/22* (2012.01)
*G06Q 50/24* (2012.01)

(52) U.S. Cl.
CPC ............... *G06Q 50/22* (2013.01); *G06Q 50/24* (2013.01)
USPC .......................................................... 705/2

(58) Field of Classification Search
USPC .......................................................... 705/2
See application file for complete search history.

(56) References Cited

U.S. PATENT DOCUMENTS

| | | | |
|---|---|---|---|
| 5,301,105 A | 4/1994 | Cummings, Jr. | |
| 5,544,044 A | 8/1996 | Leatherman | |
| 5,801,755 A * | 9/1998 | Echerer | 348/14.01 |
| 5,845,255 A * | 12/1998 | Mayaud | 705/3 |
| 6,573,887 B1 * | 6/2003 | O'Donnell, Jr. | 345/179 |
| 7,286,996 B1 | 10/2007 | Fiedotin | |
| 7,706,915 B2 | 4/2010 | Mohapatra et al. | |
| 7,711,583 B2 * | 5/2010 | Epstein et al. | 705/3 |
| 2003/0149594 A1 | 8/2003 | Beazley | |
| 2003/0191667 A1 | 10/2003 | Fitzgerald | |
| 2003/0191669 A1 | 10/2003 | Fitzgerald | |
| 2003/0195771 A1 | 10/2003 | Fitzgerald | |
| 2004/0128165 A1 | 7/2004 | Block | |
| 2004/0172289 A1 | 9/2004 | Kozic et al. | |
| 2004/0172295 A1 * | 9/2004 | Dahlin et al. | 705/2 |
| 2005/0091083 A1 | 4/2005 | McGuigan et al. | |
| 2006/0224405 A1 | 10/2006 | White et al. | |
| 2007/0033075 A1 | 2/2007 | Hoffman | |

OTHER PUBLICATIONS

Non-Final Office Action mailed Sep. 14, 2010 in U.S. Appl. No. 12/020,365.
Final Office Action mailed Jan. 5, 2011, in U.S. Appl. No. 12/020,365.

* cited by examiner

*Primary Examiner* — Michael Fuelling
(74) *Attorney, Agent, or Firm* — Shook, Hardy & Bacon L.L.P.

(57) ABSTRACT

Systems and methods are provided for accessing medication claims data and converting medication claims to active medications. In one method, medication claims data corresponding with a number of medication claims is accessed. The medication claims may then be presented to a clinician, who may manually review and determine the claims that a patient may currently be taking. Accordingly, a medication claim may be selected and converted to an active medication. A clinician may wish to convert a medication claim to an active medication for record purposes, such as for interaction checking, for example, and/or may wish to convert a medication claim to an active medication to manage the medication for the patient.

9 Claims, 6 Drawing Sheets

FIG. 5.

| | | | |
|---|---|---|---|
| PAST PRESCRIPTIONS | | | SHOW / HIDE ALL DETAILS |
| ATORVASTATIN (BRAND A) – SHOW CLAIMS \| SHOW PREVIOUS Rx | | | |
| LOVASTATIN (BRAND B) – SHOW CLAIMS \| SHOW PREVIOUS Rx | | | |
| OXYCODONE (BRAND C) – SHOW CLAIMS \| SHOW PREVIOUS Rx | | | |
| PROPRANOLOL – SHOW CLAIMS \| SHOW PREVIOUS Rx | | | |
| RECENT CLAIMS | MANAGED BY (PRESCRIBER/ORG.) | Rx DATE | SHOW / HIDE ALL DETAILS |
| | | | RENEWAL STATUS |
| ERYTHROMYCIN (BRAND D) – SHOW CLAIMS \| SHOW PREVIOUS Rx | | | |
|   BRAND D (ERYTHROMYCIN) 333 MG ENTERIC COATED TABLET | KOLM | 01-02-2005 | MANAGE/RECORRD |
|   1 EACH ORALLY EVERY 8 HOURS, DISPENSED: 30 | | | |
| PREDNISONE – SHOW CLAIMS \| SHOW PREVIOUS Rx | | | |
| C  PREDNISONE 20 MG TABLET | MCCALLIE | 11-05-2004 | MANAGE/RECORRD |
|   1 EACH ORALLY TUTHSA, DISPENSED: 15 | | | |
| C  PREDNISONE 10 MG TABLET | MCCALLIE | 11-05-2004 | MANAGE/RECORRD |
|   1 EACH ORALLY MOWEFR, DISPENSED: 15 | | | |
| C  PREDNISONE 10 MG TABLET | JONES | 10-02-2004 | MANAGE/RECORRD |
|   1 EACH ORALLY MOWEFR, DISPENSED: 15 | | | |
| C  PREDNISONE 20 MG TABLET | JONES | 10-02-2004 | MANAGE/RECORRD |
|   1 EACH ORALLY TUTHSA, DISPENSED: 15 | | | |
| C  PREDNISONE 10 MG TABLET | JONES | 09-05-2004 | MANAGE/RECORRD |
|   1 EACH ORALLY MOWEFR, DISPENSED: 15 | | | |
| C  PREDNISONE 20 MG TABLET | JONES | 09-05-2004 | MANAGE/RECORRD |
|   1 EACH ORALLY TUTHSA, DISPENSED: 15 | | | |
| PROPRANOLOL – SHOW CLAIMS \| SHOW PREVIOUS Rx | | | |
| P  PROPRANOLOL 40 MG TABLET | MCCALLIE | 11-05-2004 | MANAGE/RECORRD |
|   1 EACH ORALLY 2 TIMES A DAY, DISPENSED: 33 | | | |
| P  PROPRANOLOL 40 MG TABLET | JONES | 10-05-2005 | MANAGE/RECORRD |
|   1 EACH ORALLY 2 TIMES A DAY, DISPENSED: 35 | | | |
| P  PROPRANOLOL 40 MG TABLET | JONES | 09-05-2004 | MANAGE/RECORRD |
|   1 EACH ORALLY 2 TIMES A DAY, DISPENSED: 30 | | | |
| SILDENAFIL (BRAND E) – SHOW CLAIMS \| SHOW PREVIOUS Rx | | | |
| C*  BRAND E (SILDENAFIL) 100 MG TABLET | JONES | 12-20-2004 | MANAGE/RECORRD |
|   1 EACH ORALLY PRN: INTERCOURSE, DISPENSED: 6 | | | |
| C*  BRAND E (SIDELAFIL) 100 MG TABLET | JONES | 10-15-2004 | MANAGE/RECORRD |
|   I EACH ORALLY, PRM: INTERCOURSE, DISPENSED: 6 | | | |

FIG. 6.

CURRENT MEDICATIONS

| | MANAGED BY (PRESCRIBER.ORG) | Rx DATE | RENEWAL STATUS | |
|---|---|---|---|---|
| ATORVASTATIN (BRAND A) – SHOW CLAIMS I SHOW PREVIOUS Rx | | | | |
| Rx PA !! BRAND A (ATORVASTATIN) 40 MG TABLET<br>1 EACH ORALLY ONCE A DAY 30 DAYS, +4 REFILLS<br>INDICATION: LIPID METABOLISM DISORDER | MCCALLIE BEACON HLTH | 08-15-2004 | +15 DAYS REMAIN | Rx I DETAILS I DONE |
| GABAPENTIN (BRAND B) – SHOW CLAIMS I SHOW PREVIOUS Rx | | | | |
| Rx C !! BRAND B (GABAPENTIN) 300 MG CAPSULE<br>2 EACH ORALLY TWICE A DAY 30 DAYS, +4 REFILLS | MCCALLIE BEACON HLTH | 08-15-2004 | +15 DAYS REMAIN | Rx I DETAILS I DONE |
| PROPRANOLOL (BRAND C) – SHOW CLAIMS I SHOW PREVIOUS Rx | | | | |
| Rx* P !! BRAND C (PROPRANOLOL) 40 MG ORAL TABLET<br>1 EACH ORALLY 2 TIMES A DAY 30 DAYS, =2 REFILLS<br>INDICATION: CARDIAC DYSRHYTHRNIA NOS | MCCALLIE BEACON HLTH | 12-01-2004 | +2 MONTHS REMAIN | Rx I DETAILS I DONE |
| PREDNISONE – SHOW CLAIMS I SHOW PREVIOUS Rx | | | | |
| Rx C PREDNISONE 10 MG TABLET<br>3/DAY FOR 4 DAYS, THEN 2/DAY FOR 3 DAYS, THEN 1/DAY FOR 3 DAYS ORALLY, NO REFILLS | WALD BEACON HLTH | 12-01-2004 | +2 WEEKS REMAIN | Rx I DETAILS I DONE |
| SILDENAFIL (BRAND D) – SHOW CLAIMS I SHOW PREVIOUS Rx | | | | |
| Rx C* BRAND D (SILDENAFIL) 100 MG TABLET<br>½ TAB ORALLY, PRN: INTERCOURSE, +3 REFILLS<br>INDICATION: INHIBITED SEXUAL EXCITEMENT<br>COMMENT: CIALIS CAUSED BACK PAIN | SMITH URBAN UROLOGY | 08-15-2004 | PRN | Rx I DETAILS I DONE |
| CLEMASTINE (BRAND E) – SHOW CLAIMS I SHOW PREVIOUS Rx | | | | |
| OTC C !! BRAND E ALLERGY (CLEMASTINE) 1.34 MG TABLET<br>2 EACH ORALLY 2 TIMES A DAY, PRN: HAY FEVER<br>INDICATION: ALLERGIC RHINITIS | SELF | 12-01-2004 | OTC | Rx I DETAILS I DONE |
| CITALOPRAM (BRAND F) [CLAIM ONLY] – SHOW CLAIMS I SHOW PREVIOUS Rx | | | | |
| Cx C !! BRAND F (CITALOPRAM) 20 MG TABLET<br>#120 | JOHNSON LOOKOUT MTN MEDICAL | 03-02-2005 | | Rx I DETAILS I DONE |

PAST PRESCRIPTIONS

ATORVASTATIN (BRAND A) – SHOW CLAIMS I SHOW PREVIOUS Rx
LOVASTATIN (BRAND G) – SHOW CLAIMS I SHOW PREVIOUS Rx

CONVERTING MEDICATION CLAIMS TO ACTIVE MEDICATIONS

CROSS-REFERENCE TO RELATED APPLICATIONS

This application claims the benefit of U.S. Provisional Application No. 60/886,744, filed Jan. 26, 2007. This application is also related by subject matter to the invention disclosed in the commonly assigned application U.S. application Ser. No. 12/020,365, filed on even date herewith, entitled "SYSTEM-DETERMINED INDICATION FOR FACILITATING THE CONVERSION OF MEDICATION CLAIMS TO ACTIVE MEDICATIONS."

STATEMENT REGARDING FEDERALLY SPONSORED RESEARCH OR DEVELOPMENT

Not applicable.

BACKGROUND

Prescribing medications to patients is often a complex practice for clinicians, with patients often visiting multiple prescribing clinicians and a continuously increasing number of available medications. The growing complexity of prescribing medications has given rise to an increased risk of medication errors. For example, without proper information, a clinician may prescribe a medication having an adverse interaction with a medication prescribed by another clinician. In addition, a clinician may inadvertently duplicate a medication already prescribed by another clinician.

Accordingly, information detailing what medications a patient is currently taking or has taken in the past may be invaluable to a clinician treating the patient. Such medication information may be available via a patient's medication profile or a medical record, such as a community health record, electronic medical record, or personal health record, for example. Unfortunately, in many circumstances, information detailing a patient's current medications and/or medication history may not be readily available to the clinician treating the patient. For example, in some cases, a medication profile or medical record may not be available for the patient. In other cases in which a medication profile or medical record is available, the profile or record may either provide incomplete medication information or completely fail to provide any medication information at all. In such instances, a clinician may question a patient regarding current and past medications. However, the patient may not know details regarding his/her medications or may provide inaccurate information.

One potential source of medication information for patients may be medical claims data. Payers involved in the business side of healthcare, including insurance companies, claims processing companies, and the like, all have the potential to produce medical claims data as part of their normal business operation. This claims data may be for any of a variety of healthcare-related services, including medications. Typically, a payer may have medication claims data representing years worth of medication utilization information that is tied to each patient. However, there is currently no convenient solution for clinicians to access medication claims information for patients and use the information to populate and/or replenish a medications profile or medical record for each patient.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to converting medication claims to active medications such that clinicians may document and manage the medications. Accordingly, in one aspect, the present invention is directed to a method in a clinical computing environment for converting medication claims to active medications. The method includes accessing medication claims data providing information for one or more medication claims. The method also includes presenting the one or more medication claims and receiving a selection of one of the one or more medication claims. The method still further includes converting the selected medication claim to an active medication based on the selection.

In another aspect of the invention, embodiments further relate to a system in a clinical computing environment for converting medication claims to active medications. The system includes a medication claims data accessing component, a presentation component, a selection receiving component, and a conversion component. The medication claims data accessing component is capable of accessing medication claims data providing information for one or more medication claims. The presentation component is capable of presenting the one or more medication claims. The selection receiving component is capable of receiving a selection of one of the one or more medication claims. The conversion component is capable of converting the selected medication claim to an active medication based on the selection.

In a further aspect, an embodiment of the present invention is directed to one or more computer-readable media having computer-useable instructions embodied thereon that provide for the presentation of one or more user interfaces for facilitating the conversion of a medication claim to an active medication. The one or more user interfaces include a medication claims area and a current medications area. The medication claims area comprises a list of one or more medication claims and provides for a user selection of medication claims for conversion to active medications. The current medications area comprises a list of one or more current medications, which includes active medications converted from medication claims.

BRIEF DESCRIPTION OF THE DRAWINGS

The present invention is described in detail below with reference to the attached drawing figures, wherein:

FIG. 5 is an illustrative screen display of an exemplary user interface for reviewing medication claims and selecting medication claims for conversion to active medications in accordance with an embodiment of the present invention;

FIG. 6 is a screen display of an exemplary user interface showing current medications including a medication claim that has been converted to an active medication in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide computerized methods and systems for accessing medication claims data for patients and allowing a clinician to manually review and convert a medication claim to an active medication. By converting a medication claim to an active medication, the clinician may manage the active medication similar to the way the clinician manages other medications that the clinician has prescribed. In some cases, the clinician may not wish to manage the medication, but may wish to convert the medication claim to an active medication for documentation and recording purposes. Accordingly, embodiments of the present invention, among other things, may allow for populating and/or replenishing medication profiles for patients for both management and documentation purposes Embodiments of the present invention further provide computerized methods and systems for automatically determining claims associated with medications that a patient may be currently taking and providing an indication for these claims. A clinician may then easily review the medication claims, readily identify medication claims associated with medications that may be current, and manually convert particular medication claims to active medications.

As used herein, the terms "individual", "person", and "patient" are used interchangeably and are not meant to limit the nature of the referenced individual in any way. Rather, the methods and systems described herein are equally applicable in, for instance, a veterinary setting. Further, use herein of the term "patient" is not meant to imply any particular relationship between the individual in question and those accessing, updating, and/or viewing the patient's information.

Figure 1:
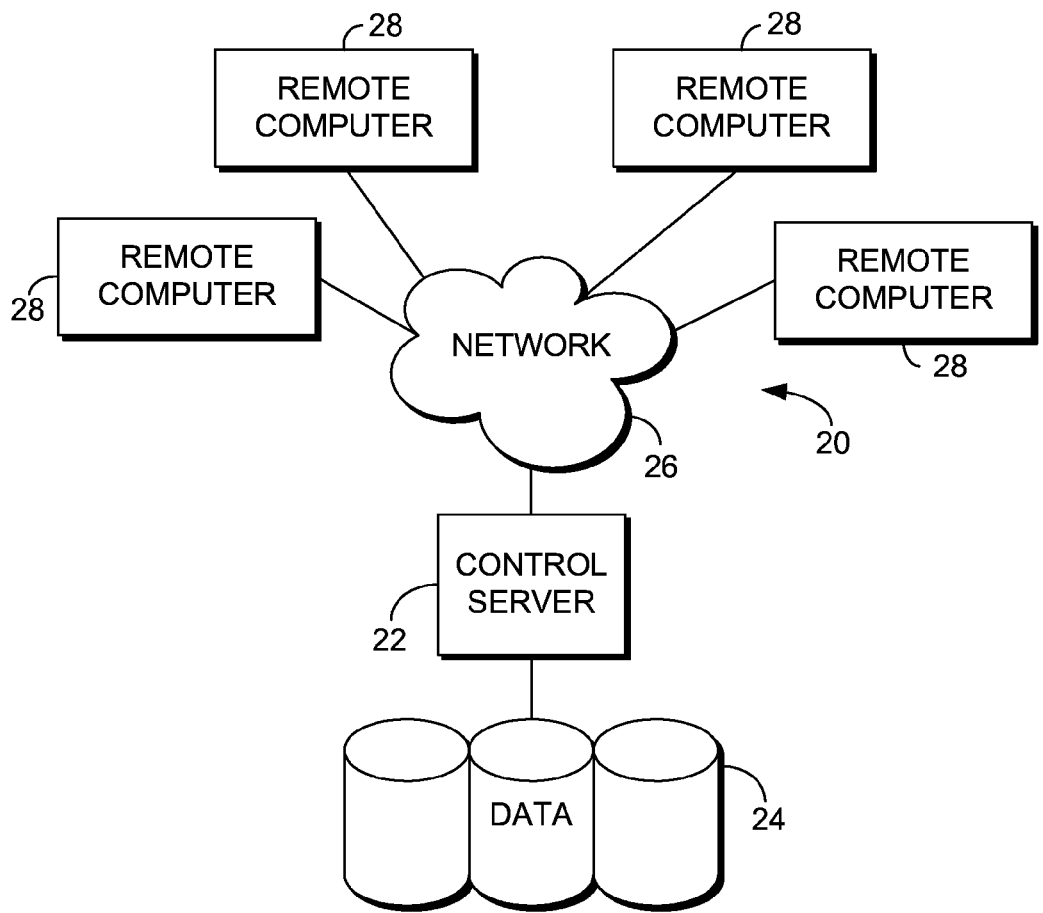
FIG. 1 is a block diagram of an exemplary computing environment suitable for use in implementing the present invention.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 2:
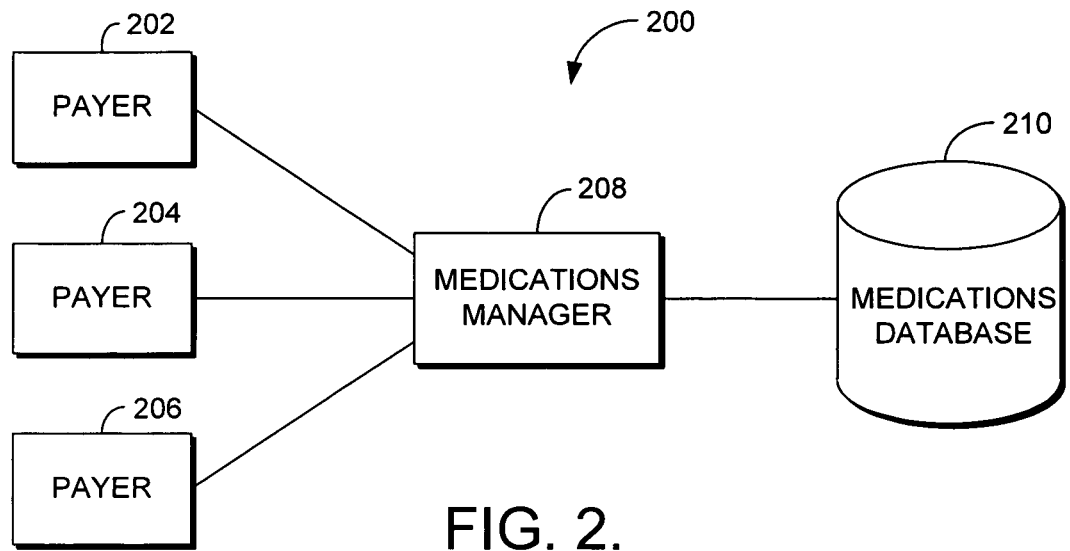
FIG. 2 is a block diagram of an exemplary system for accessing medication claims data and making the medication claims available for conversion to active medications in accordance with an embodiment of the present invention.

With reference to FIG. 2, a block diagram is provided showing a system 200 for accessing medication claims data and making the data available for converting medication claims to active medications. As shown in FIG. 2, medication claims data may be accessed from a variety of payers, such as the payers 202, 204, and 206. As used herein, the term "payer" refers to any entity maintaining medication claims data, such as an insurance company or a claims processing company, for example. Although only three payers are shown in FIG. 2, it should be understood that medication claims data may be accessed from any number of payers within the scope of the present invention.

A medications manager 208 may be in communication with each of the payers 202, 204, 206 and may access medication claims data from each respective payer. The medications manager 208 and payers 202, 204, 206 may communicate via one or more networks, which may comprise one or more wide area networks (WANs) and one or more local area networks (LANs), as well as one or more public networks, such as the Internet, and one or more private networks. In various embodiments of the present invention, a payer may upload medication claims data to the medications manager 208, and/or the medications manager 208 may pull medication claims data from a payer.

Medication claims data accessed by the medications manager 208 may include a wide variety of data elements, such as medication name, generic name, dosage, quantity dispensed, and date dispensed, for example. The data elements available for each medication claim may vary widely, with some medication claims having more data elements available than others. In addition, medication claims data may reside in a native format that differs from payer to payer. Accordingly, in some embodiments of the present invention, it may be necessary to convert medication claims data from the various payers to a standard format such that common data elements may be recognized. As such, after accessing medication claims data, the medications manager 208 may determine whether data formatting is required. If so, the medications manager 208 may map data elements to a standard format useable by embodiments of the present invention. For example, in some embodiments, the medications manager 208 may determine an appropriate data mapping based on the source of medication claims data.

A database, such as the medications database 210, may be provided for storing medication claims data accessed by the medications manager 208. For example, after the medications manager 208 converts medication claims data to a standard format, it may populate the medications database 210 with the information. As a result, medication claims data is available in a standardized format for review and conversion to active medications. In some embodiments, the medications manager 208 may be in communication with a medications profile or electronic medical record (e.g., a community health record or a personal health record) and may populate the profile or record with the medications claims data such that the medication claims data may be reviewed in conjunction with other available information regarding a patient's current medication usage and medications history.

Figure 3:
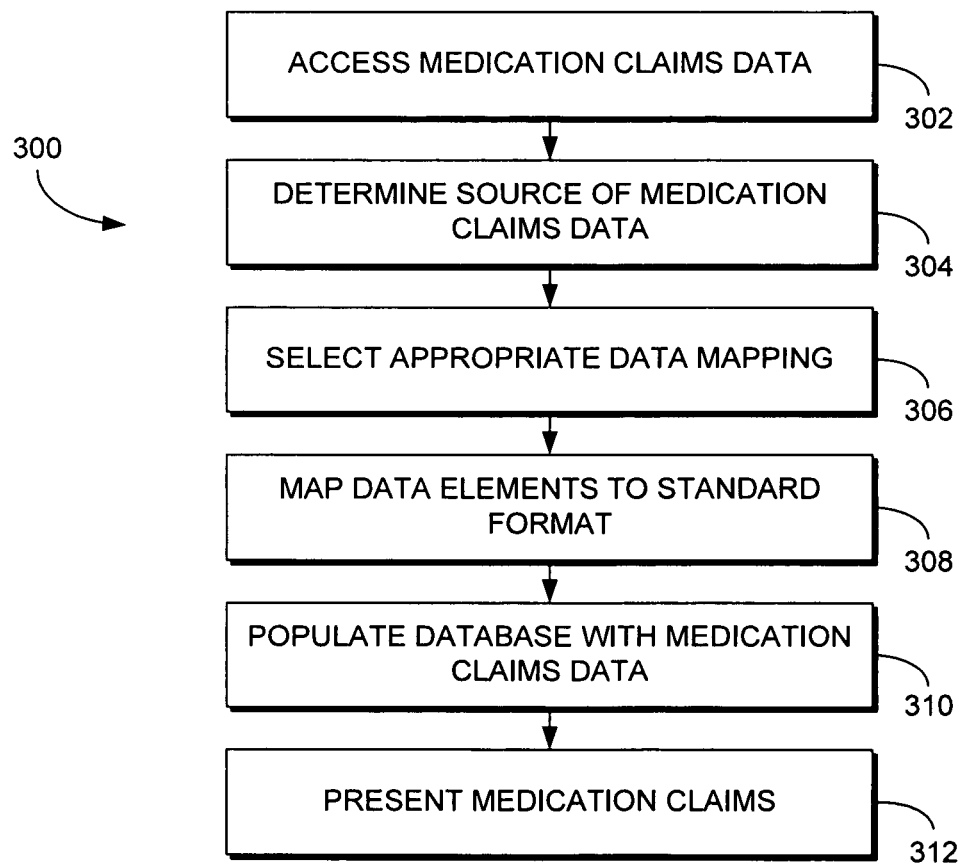
FIG. 3 is a flow diagram showing a method for accessing medication claims data and presenting the data, for instance, to a clinician in accordance with an embodiment of the present invention.

Turning now to FIG. 3, a flow diagram is provided illustrating a method 300 for accessing medication claims data and presenting the data to a clinician in accordance with embodiments of the present invention. Initially, medication claims data may be accessed, as shown at block 302. As mentioned previously, medications claims data may be uploaded by payers to a medications manager, such as the medications manager 208 of FIG. 2, and/or may be pulled from the payers by the medications manager.

Because medication claims data received from various payers may include different data elements and formatting, some embodiments of the present invention convert the data to a standard format. Accordingly, after accessing medication claims data, the source of the data may be determined, as shown at block 304. Based on the source of the data, an appropriate data mapping may be selected to convert data elements of the medication claims, as shown at block 306. Data elements of the medication claims data may then be mapped to the standard format, as shown at block 308. A database, such as the medications database 210 of FIG. 2, a medication profile, or an electronic record may then be populated with the properly formatted medication claims data, as shown at block 310.

Based on the accessed medication claims data, a listing of medication claims may be presented to a clinician, as shown at block 312. This may comprise a user interface through which a clinician may review medication claims and select particular claims for conversion to active medications. Although medication claims data may be available for a significant period of time, a clinician may typically only be interested in reviewing the most recent medication claims. Accordingly, in some embodiments, medication claims information may be filtered such that only recent medication claims are displayed to the clinician. For example, only claims from the most current three month period may be displayed in the user interface.

In some embodiments, if medication information is available from other sources, such as a medication profile or an electronic medical record, both the medication claims and the otherwise available medication information may be presented to the clinician, thereby providing a more complete picture regarding a patient's current and historical medication usage. Further, in some embodiments, interaction checking may be performed to determine whether any adverse interactions exist among the various medications included in the medication claims data and/or the medication information. An interaction alert may then be provided for any adverse interactions detected.

Figure 4:
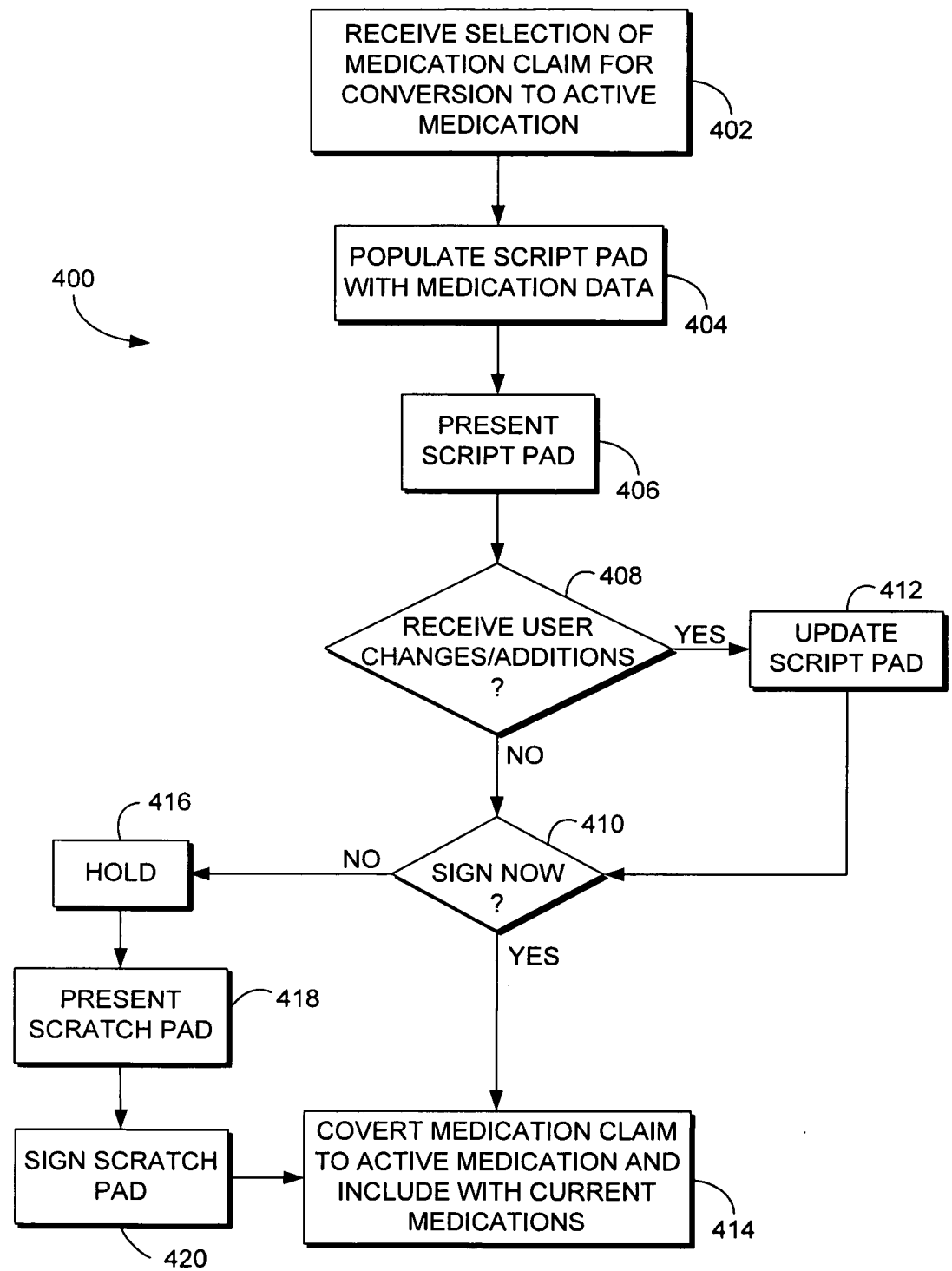
FIG. 4 is a flow diagram showing a method for converting a medication claim to an active medication in accordance with an embodiment of the present invention.

A clinician may review the medication claims and determine whether any claim should be converted to an active medication for documentation and management purposes. For example, in some cases, the clinician may wish to manage a medication associated with a particular medication claim in the same way the clinician may manage medications that he/she has prescribed for a patient. In other cases, a clinician may not need to manage a medication associated with a particular medication claim but may wish to include the medication with other current medications for the purpose of providing alerts, interaction checking, and the like. Accordingly, a flow diagram showing a method 400 for converting a medication claim to an active medication in accordance with an embodiment of the present invention will now be described with reference to FIG. 4.

Initially, as shown at block 402, a clinician selects a medication claim for conversion to an active medication. Based on the selection, a script pad is populated with information regarding the particular medication, as shown at block 404. The script pad may be populated with data from a variety of different sources. For example, medication claims data for the selected medication claim may be used to populate the script pad. In addition, the script pad may be populated using information relating to preferences for prescribing the medication. Further, information regarding how the medication is commonly prescribed may be used to populate the script pad. In some embodiments, a preference may be established for the source of data used to populate the script pad. Any and all such variations are contemplated to be within the scope of embodiments of the present invention.

After being populated with data, the script pad is presented to the clinician, as shown at block 406. The clinician may then review and validate the information populated in the script pad, thereby determining whether any changes or additional information are necessary, as represented at block 408. If no changes or additions are made, the clinician may choose to electronically sign the script pad, as shown at block 410. Alternatively, if changes and/or additions are required, the clinician may enter additional data or make changes, and the script pad is accordingly updated, as shown at block 412. The clinician may then chose to sign the script pad. Once the clinician signs the script pad, the medication claim is converted to an active medication and included as a current medication, as shown at block 414.

In some cases, the clinician may choose not to sign the script pad at block 410. For example, the clinician may be handling multiple medications at one time and may wish to sign all medications at one time. In such a case, the script pad is held, as shown at block 416. Once the clinician is ready to sign, a scratch pad is presented, as shown at block 418. The clinician may then sign the scratch pad, as shown at block 420, and any included medication claims are then converted to active medications.

Referring now to FIGS. 5 and 6, embodiments of the present invention are further described with reference to user interfaces that may be employed for converting medication claims to active medications and managing current medications. It will be understood and appreciated by those of ordinary skill in the art that the screen displays of FIGS. 5 and 6 are provided by way of example only and are not intended to limit the scope of the present invention in any way.

Initially, FIG. 5 provides an exemplary screen shot of a user interface 500 presenting a list of medication claims that may be converted to active medications in accordance with an embodiment of the present invention. As shown in FIG. 5, a number of medication claims are presented to the clinician in a recent claims area 502. Claims may be grouped together based on generic substance of medication, and a variety of information may be associated with each claim and presented in the user interface 500. By way of example only and not limitation, information presented for each medication claim may include the clinician who prescribed a medication, when the medication was prescribed, the quantity dispensed, and the frequency prescribed. One skilled in the art will recognize that a wide variety of additional information may be presented for each medication claim.

As discussed previously, the medication claims data may be filtered such that the user interface presents only the most recent claims. In some cases, however, a clinician may wish to view older medication claims. An actionable icon, such as icon 504, may be provided within user interface 500 for displaying all medication claims for a particular generic substance. For example, if a clinician were to select the icon 504, all claims for the generic substance, "propanolol," would be displayed.

Interaction alerts may also be presented in the user interface to indicate a potential interaction between one or more medications. For example, an interaction alert icon, such as icon 506, may be provided to indicate that the medication of a particular claim has an interaction with one or more other medications. The interaction may be with a medication associated with another medication claim or may be with a current medication. In some embodiments of the present invention, an interaction alert icon is provided as an actionable icon, such that when a user selects the icon, information is presented detailing the relevant interaction.

A clinician may review the recent medication claims provided in the user interface 500 and determine whether any claim should be converted to an active medication. In some cases, the clinician may wish to manage a medication associated with the medication claim in the same way the clinician may manage medications that he/she has prescribed for a patient. Accordingly, the user interface 500 includes a manage icon, such as the icon 508 shown in FIG. 5, with each medication claim listed in the recent claims area 502. In other cases, a clinician may wish to document a medication associated with a medication claim. For example, a clinician may not want to manage the medication but may wish to include the medication as a current medication for the purpose of providing alerts, interaction checking, and the like. As such, the user interface 500 includes a record icon, such as the icon 510, with each medication claim.

By selecting either a manage icon or a record icon, a clinician may convert the associated medication claim to an active medication. For example, a clinician may wish to manage the propanolol medication 512 and may select the corresponding manage icon 508. In response to the selection, a script pad may be populated with data regarding the propanolol medication and presented to the clinician. As indicated previously, the clinician may either sign the script pad or hold and later sign a scratch pad with multiple medications.

After an electronic signature is provided via either a script pad or scratch pad, the selected propanolol medication claim is converted to an active medication. Referring to FIG. 6, a user interface 600 is illustrated, in which a current medications area 602 provides a list of current medications, including medications that have been converted from medication claims to active medications. As shown in FIG. 6, a propanolol medication 604 has been included as a current medication.

Figure 7:
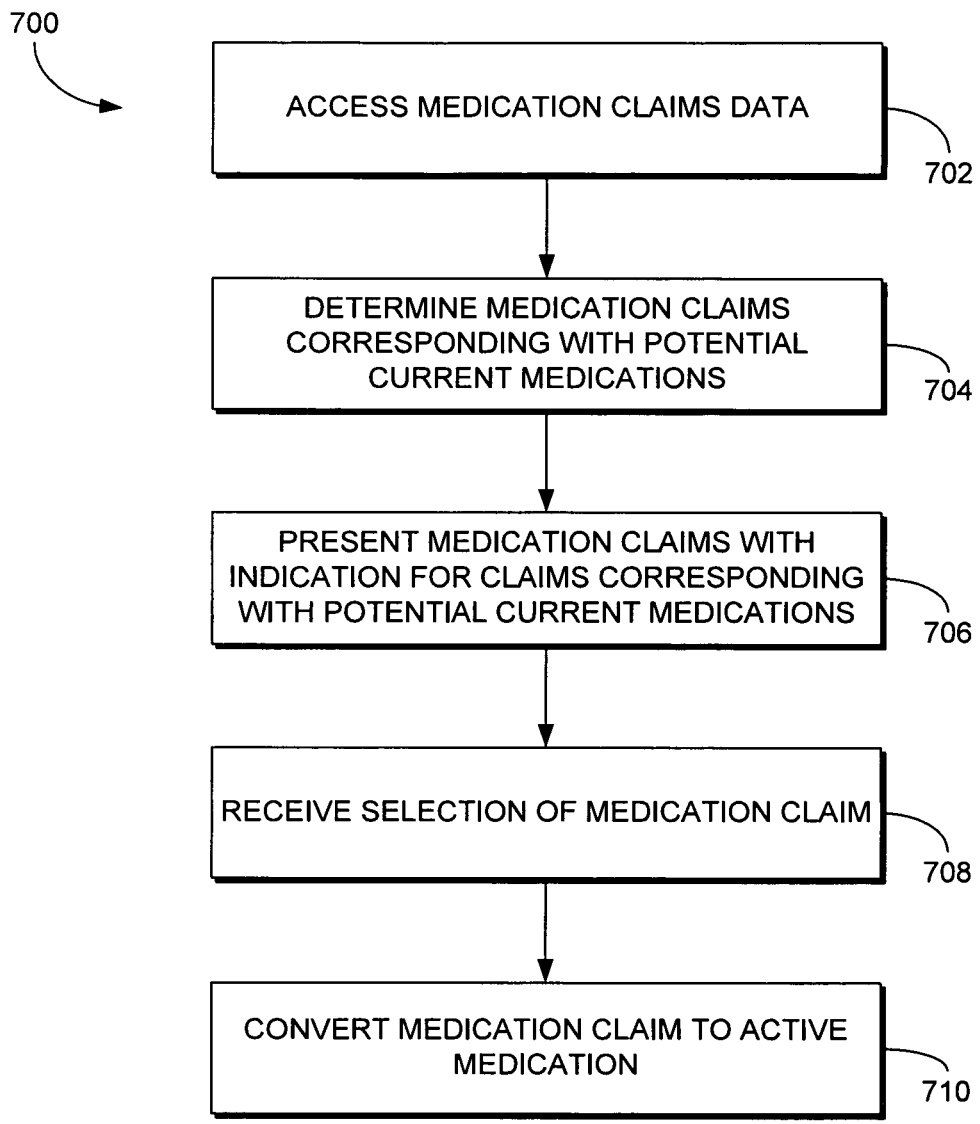
FIG. 7 is a flow diagram showing a method for facilitating the conversion of medication claims to active medications by determining and indicating medication claims corresponding with medications that a patient may be currently taking in accordance with an embodiment of the present invention.

In another embodiment of the present invention, medication claims corresponding with medications that a patient may be currently taking may be algorithmically determined and identified, thereby making it easier for a clinician to review and manually convert medications claims to active medications. Referring to FIG. 7, a flow diagram is provided illustrating a method 700 for facilitating the conversion of medication claims to active medications by determining and providing an indication of medication claims that may correspond with medications that a patient is currently taking. Initially, medication claims data is accessed, as shown at block 702. The medication claims data may be accessed from a variety of payers and converted to a standard format as previously described with reference to method 300 and FIG. 3. In some cases, medication claims data may have been previously accessed from payers, converted, and populated into a database, such as the database 210 of FIG. 2, and, accordingly, the medication claims data may be accessed from the database.

As shown at block 704, medication claims corresponding with medications that a patient may be currently taking are algorithmically determined. Any of a variety of different ways for determining whether a medication claim corresponds with a current medication may be employed within the scope of the present invention. In addition, the determination may be based on various data elements that may be included in the medication claims data, such as the type of medication, the date of service of the medication claim, the date of the prescription, the quantity of the medication dispensed, the dosage prescribed, and the frequency prescribed, for example. Additionally, the determination may employ assumptions made based on data elements included in the medication claims data and/or assumptions made to compensate for missing data elements.

By way of example only and not limitation, the determination for a particular medication claim may comprise accessing medication claims data for the claim and approximating a time period that the patient would be taking the medication. For instance, such a determination may be based on the date a medication was prescribed, the quantity dispensed, and the frequency described. Using those pieces of data, the time period that the patient is taking the medication may be approximated. If the current date is within that time period, the medication claim is accordingly determined to correspond with a current medication. As a further example, in some embodiments, the determination may be based, at least in part, upon whether the medication corresponds with an acute or chronic condition. Because medications for acute conditions (e.g., a pain medication prescribed post-surgery) are inherently short-term and will most likely not be continued after an initial prescription, clinicians may not wish to manage or record these medications. Accordingly, in some embodiments, only medications claims corresponding with medications for chronic conditions may be considered for providing an indication. Alternatively, however, some clinicians may wish to convert medication claims associated with medications for both acute and chronic conditions. Accordingly, in some embodiments, all medication claims may be considered. One skilled in the art will recognize that a wide variety of other algorithmic determinations may be employed depending upon the data available in the medication claims data.

After a determination has been made, the medication claims are presented, as shown at block 706. An indication is provided for the medication claims determined to correspond to medications that a patient may be currently taking. Any type of indication may be provided within the scope of the present invention. By way of example only and not limitation, the indication may consist of highlighting a medication claim. As another example, the indication may consist of providing an indication icon with a corresponding medication claim.

A clinician may review the medication claims and more easily identify claims for conversion to active medications based on the provided indications. Accordingly, a selection of a medication claim is received, as shown at block 708. Based on the selection, the selected medication claim is converted to an active medication and listed as a current medication, as shown at block 710. The conversion may comprise populating a script pad and signing the script pad (or a scratch pad) as previously discussed with reference to method 400 and FIG. 4.

As can be understood, embodiments of the present invention provide for the conversion of medication claims to active medications, allowing a clinician to record and/or manage medications based on medication claims data. Further embodiments of the present invention provide for automatically determining and indicating medication claims that may correspond with medications that a patient is currently taking, allowing a clinician to easily review and convert medication claims to active medications.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media having computer-executable instructions embodied thereon that, when executed facilitate a method in a clinical computing environment for converting medication claims to active medications, the method comprising:
    accessing medication claims data corresponding with one or more medication claims;
    determining a source of the medication claims data;
    selecting a data mapping based on the source; and
    mapping at least one data element of the medication claims data to a standard format;
    presenting the one or more medication claims;
    receiving a selection of one of the one or more medication claims; and
    converting the selection to an active medication by populating a script pad with medication data associated with the selected medication claim and presenting the script pad.

2. The media of claim 1, wherein accessing medication claims data comprises accessing a database storing the medication claims data.

3. The media of claim 1, wherein accessing medication claims data comprises accessing medication claims data from one or more payers.

4. The media of claim 1, wherein presenting the one or more medication claims comprises presenting a user interface providing for the selection of at least one of the one or more medication claims for conversion to the active medication.

5. The media of claim 1, further comprising, for the selection, determining whether there is an interaction with another medication claim of the one or more medication claims or a current medication, and if an interaction is determined, presenting an indication of the interaction.

6. The media of claim 1, wherein the medication data is based on at least one of the medication claims data associated with the selected medication claim, information regarding preferences for prescribing the active medication, and information regarding common choices for prescribing the active medication.

7. The media of claim 1, wherein converting the selected medication claim to an active medication further comprises receiving at least one of a change to the medication data and an addition to the medication data.

8. The media of claim 1, wherein converting the selected medication claim to an active medication further comprises receiving an electronic signature on the script pad.

9. The media of claim 1, wherein converting the selected medication claim to an active medication further comprises:
    receiving an indication to hold the script pad;
    presenting a scratch pad when prompted; and
    receiving an electronic signature on the scratch pad.

* * * * *